(12) United States Patent
Silver (10) Patent No.: US 10,004,889 B2
(45) Date of Patent: Jun. 26, 2018

(54) ENTERAL FEEDING CONNECTOR AND ASSEMBLY

(75) Inventor: Brian H. Silver, Cary, IL (US)

(73) Assignee: MEDELA HOLDING AG (CH)

( * ) Notice: Subject to any disclaimer, the term of this patent is extended or adjusted under 35 U.S.C. 154(b) by 406 days.

(21) Appl. No.: 13/189,031

(22) Filed: Jul. 22, 2011

(65) Prior Publication Data

US 2012/0022457 A1   Jan. 26, 2012

Related U.S. Application Data

(60) Provisional application No. 61/367,228, filed on Jul. 23, 2010.

(51) Int. Cl.
| | | |
|---|---|---|
| *A61M 5/31* | (2006.01) | |
| *A61M 39/10* | (2006.01) | |
| *A61J 1/20* | (2006.01) | |
| *A61J 15/00* | (2006.01) | |

(52) U.S. Cl.
CPC ...... *A61M 39/1011* (2013.01); *A61J 15/0026* (2013.01); *A61J 1/2055* (2015.05); *A61J 1/2072* (2015.05); *A61J 1/2096* (2013.01); *A61J 15/00* (2013.01); *A61M 2039/1027* (2013.01); *A61M 2039/1033* (2013.01); *A61M 2039/1094* (2013.01)

(58) Field of Classification Search
CPC ...... A61M 39/1011; A61M 2039/1027; A61M 2039/1094; A61M 2039/1033; A61J 15/0026; A61J 1/2055; A61J 1/2072; A61J 15/00; A61J 1/2096; A61J 1/2075

USPC ....... 604/181, 187, 535, 537, 538, 257, 533, 604/534
See application file for complete search history.

(56) References Cited

U.S. PATENT DOCUMENTS

| | | | | |
|---|---|---|---|---|
| 2,870,765 | A * | 1/1959 | Henderson | 604/242 |
| 3,729,031 | A * | 4/1973 | Baldwin | A61M 5/1782 141/2 |
| 4,266,815 | A * | 5/1981 | Cross | 285/330 |
| 4,787,892 | A | 11/1988 | Rosenberg | |
| 4,994,029 | A * | 2/1991 | Rohrbough | A61M 5/2429 206/222 |
| 5,071,413 | A * | 12/1991 | Utterberg | A61M 5/162 604/411 |
| 5,139,483 | A * | 8/1992 | Ryan | A61M 39/1011 604/533 |
| 5,356,396 | A * | 10/1994 | Wyatt | A61M 39/04 604/539 |
| 5,500,014 | A | 3/1996 | Quijano et al. | |
| 5,609,584 | A * | 3/1997 | Gettig | A61M 5/3134 604/535 |
| 5,620,433 | A | 4/1997 | Aswad et al. | |

(Continued)

OTHER PUBLICATIONS

International Search Report and Written Opinion for International App. No. PCT/US2011/045026, completed Nov. 2, 2011.

(Continued)

*Primary Examiner* — Theodore Stigell
(74) *Attorney, Agent, or Firm* — McDonnell Boehnen Hulbert & Berghoff LLP (57) ABSTRACT

A connector for use with a syringe or extension tubing, such as an enteral feeding syringe or tubing, is provided. The connector has features to effectively secure a syringe or extension tubing with the connector without contamination from a user.

8 Claims, 8 Drawing Sheets

(56) References Cited

U.S. PATENT DOCUMENTS

| | | |
|---|---|---|
| 6,193,697 B1 * | 2/2001 | Jepson et al. .................. 604/201 |
| 6,332,467 B1 | 12/2001 | Hutson et al. |
| 6,565,541 B2 * | 5/2003 | Sharp ............................ 604/192 |
| 6,582,388 B1 | 6/2003 | Coleman et al. |
| 6,585,718 B2 | 7/2003 | Hayzelden et al. |
| 7,534,224 B2 | 5/2009 | Triebes et al. |
| 2008/0312594 A1 | 12/2008 | Urich et al. |
| 2009/0184275 A1 * | 7/2009 | Ruschke et al. ........... 251/149.1 |

OTHER PUBLICATIONS

International Search Report and Written Opinion for International App. No. PCT/US2011/045032, completed Nov. 6, 2011.
U.S. Appl. No. 13/189,023, filed Jul. 22, 2011 to Silver.

\* cited by examiner

ENTERAL FEEDING CONNECTOR AND ASSEMBLY

1. CROSS-REFERENCE TO RELATED APPLICATIONS

This application is a non-provisional of U.S. Provisional Patent Application Ser. No. 61/367,228 filed Jul. 23, 2010, entitled "Enteral Feeding Connector and Assembly", the contents of which are fully incorporated herein by reference.

2. FIELD OF THE INVENTION

The present invention relates generally to tubing connectors, and more particularly in one aspect to an enteral feeding assembly including an improved syringe and connector.

3. BACKGROUND OF THE INVENTION

Fluid delivery systems, such as feeding tubes, are used to deliver nutrients and medicine to patients. The state of being fed by a feeding tube is known in the art as enteral feeding or tube feeding.

As an example, in a neo-natal unit, infants are often fed enterally. A tube is inserted in the mouth or nasal opening of the infant and through the esophagus for delivery of the fluid to the stomach or intestinal region of the body. In this example, breast milk or formula are delivered by syringe into an enteral delivery system, such as an enteral tube, for delivery into the infant's stomach. However, enteral feeding systems can also be for pediatric or adult use. Sometimes a peristaltic pump is used to deliver fluids from a feeding bag.

Bacterial contamination of enteral feeding equipment is a problem. Although current American Society for Parenteral and Enteral Nutrition ("ASPEN") guidelines tell care givers to use gloves when handling enteral feeding connections, often these guidelines are not followed, and contamination can occur due to handling of the feeding components by a care giver. The care giver may compromise either the tube or the syringe tip by touching those parts, as the care giver attempts to attach the tube to the syringe tip, for instance. However, contamination is not limited to the hands of a care giver, as anything that touches the tube or syringe tip can potentially contaminate either part. Luer lock connection devices have been used to connect two parts to each other, for example. A luer lock typically comprises a screw or thread lock mechanism used to axially fit a male part within a female part to secure two parts to each other. These parts are typically exposed to being handled by the user.

Furthermore, a lack of air circulation and fluid draining areas in the fluid delivery system may promote bacterial growth.

A contaminated enteral feeding system may lead to problems for the patient, resulting in diarrhea, vomiting, pneumonia, urinary tract infections, septicaemia, as well as gastrointestinal infections or weight loss of the patient.

SUMMARY OF THE INVENTION

An improved connector for use with a syringe, enteral feeding tube, or extension set is provided. The connector comprises a tube with a first end, a second end, and an exterior surface. The connector defines a gripping portion on the exterior of the tube and an attachment portion. The gripping portion is designed to protect the ends of the connector, and thus the liquid path, from being touched or otherwise compromised.

In another aspect, the attachment portion has a locking feature, which positively attaches the connector to the syringe. That is, the locking feature is more than a typical interference engagement or luer lock.

In an embodiment, a connector for use with a complementary syringe is provided. A connector tube has a first end and a second end and an exterior. The tube contains a conduit therein, and has a portion(s) so as to protect against contact with the conduit ends by a user. An attachment portion of the connector tube has a locking feature, and the locking feature attaches the connector to the syringe. The locking feature in various embodiments is a threaded engagement, or a latching connection. In the latching engagement, the connector tube cannot be disengaged except by moving the latch, i.e., the connector tube cannot be simply pulled free.

In yet another embodiment, a connector for use with a complementary syringe is provided. A connector tube has a first end and a second end and an exterior. The connector contains a conduit therein, and has a gripping part spaced from the conduit so as to protect against contact with the conduit ends by a user. An attachment portion of the connector tube attaches the connector to the syringe, as by way of a slip or interference fit.

These and other aspects, objects, and accomplishments of the present invention will be further understood upon consideration of the following detailed description of certain embodiments, taken in conjunction with the below drawings depicting various embodiments, in which:

BRIEF DESCRIPTION OF THE DRAWINGS

Various exemplary embodiments are described herein with reference to the following drawings, wherein like numerals denote like parts.

DETAILED DESCRIPTION OF THE DRAWINGS

The connector and assembly of the present invention will be described herein for use with an enteral feeding tube, but it is contemplated that the connector assembly of the present invention can be used in any device that may benefit from this type of connector.

Figure 1:
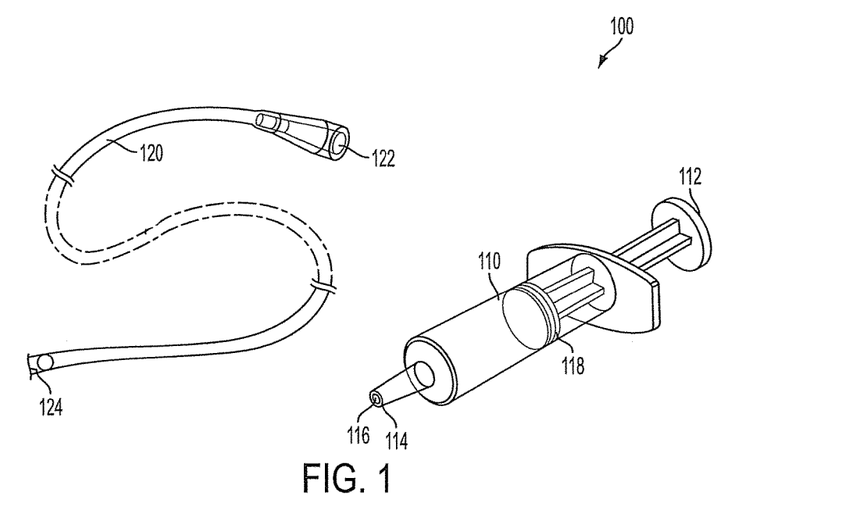
FIG. 1 is a perspective view of an enteral feeding system.

FIG. 1 is a perspective view of a typical enteral feeding system 100, in accordance with exemplary embodiments. Enteral feeding system 100 has a syringe 110 and a tube 120. Syringe 110 has a distal end 112, a proximal end 114, and a plunger 118. At proximal end 114 is a syringe tip 116. Tubing 120 has a first end 122 and a second end 124. In this system 100, first end 122 of tube 120 and syringe tip 116 may be removably secured together. To secure syringe tip 116 to first end 122 of tube 120, syringe tip 116 is manually inserted into first end 122 of tube 120.

The direct manipulation of both syringe tip 116 and first end 122 of tube 120 can result in exposure to contamination. Because fluid flows from syringe 110 and through tube 120 into a patient, if either syringe tip 116 or first end 122 of tube 120 are contaminated, a patient may be exposed to the contamination. Similarly, exposure of syringe tip 116 or tube 120 to the environment alone can result in contamination of the fluid that flows through either piece. Furthermore, the simple interference fit of the tubing 120 on the syringe tip can be easily, and unintentionally, disengaged.

Figure 2:
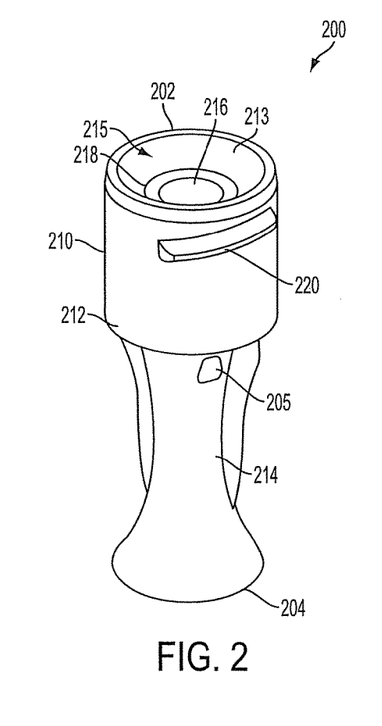
FIG. 2 is a perspective view of an inventive connector that may be used with the enteral feeding system illustrated in FIG. 1.

FIG. 2 is a perspective view of a connector 200 of the present invention that may be used with an enteral feeding system in accordance with an exemplary embodiment. Connector 200 has an exterior surface 210, a first end 202, a second end 204, and at least one vent 205. The exterior surface 210 includes two portions: an attachment portion 212 and a gripping portion 214.

Attachment portion 212 has an interior surface 213 with a sidewall 218 that defines an aperture 215 with an internal conduit 216. Internal conduit 216 may take the shape of a tube with a bore defined therethrough. Internal conduit 216 extends through attachment portion 212 and gripping portion 214, and serves as a conduit for conducting fluids. The bore of internal conduit 216 is sized to match an outer diameter of a syringe tip, such as that of the syringe described below and shown in FIG. 3. Thus, internal conduit 216 serves as a female connector, sized to receive a syringe tip at first end 202. Second end 204 is shown flared outwardly to surround a nipple 206 (shown in FIG. 4), which will receive an enteral tube 120 end thereon.

The at least one vent 205 serves to keep the inside of connector 200 dry, for instance, if liquid has leaked into the connector. By keeping the inside of connector 200 dry, bacterial growth may be inhibited.

In one embodiment, exterior surface 210 of attachment portion 212 may have a locking feature 220. In this embodiment, locking feature 220 may comprise a protrusion or flange that extends circumferentially about part of exterior surface 210, although the protrusion may extend at an angle in relation to the circumference (like a screw thread). Locking feature 220 is sized and shaped to correspond with a groove of the interior surface of the syringe, as hereafter described.

Figure 3:
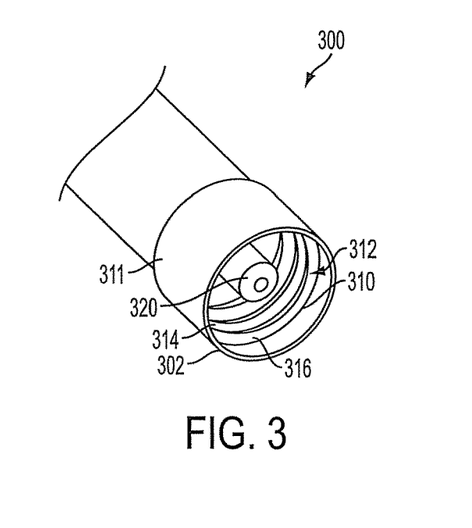
FIG. 3 is a partial, perspective view of the second end of a syringe, such as the syringe of FIG. 1.

FIG. 3 is a partial, perspective view of the proximal end of a syringe 300, like the syringe 110 of FIG. 1. As can be seen in FIG. 3, at the proximal end 302 of syringe 300 is a shroud 311 comprising an interior surface 310 that defines a well 312. Interior surface 310 of shroud 311 also comprises screw threads 314 that turn along the interior circumference of well 312 to define a spiral groove 316. A syringe tip 320 extends within well 312, but does not extend as far as proximal end 302. In an alternative embodiment, syringe tip 320 may extend as far or further than proximal end 302. Shroud 311 may be integrally molded as part of syringe 300, or in the alternative shroud 311 may be manufactured as a separate part that is later attached to syringe 300.

In an alternative configuration, no locking feature is present on connector 200, and connector 200 may simply fit within syringe 300 by way of a slip or interference fit. This will be further discussed with respect to FIGS. 16-18 and their "no-touch" aspect.

Figure 4:
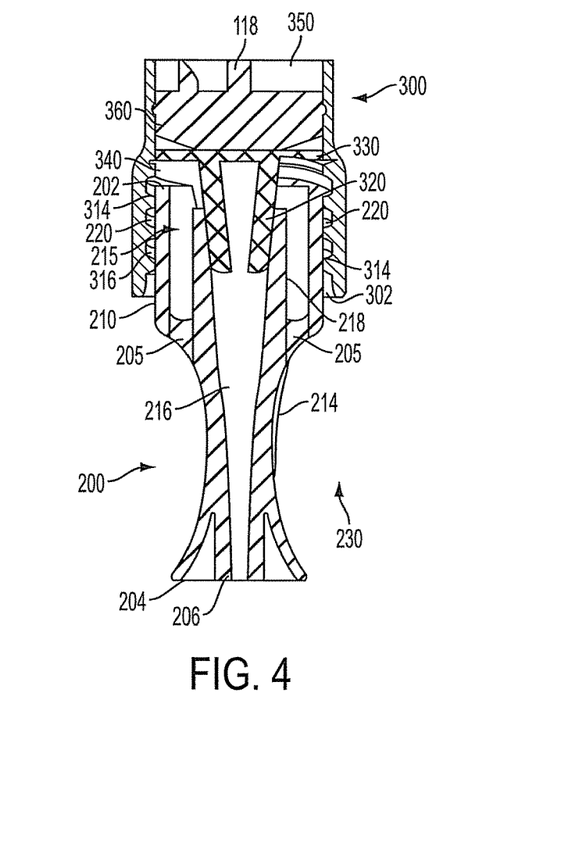
FIG. 4 is an assembled cross-sectional view of the connector of FIG. 2 within the syringe of FIG. 3, in accordance with an exemplary embodiment.
Figure 5:
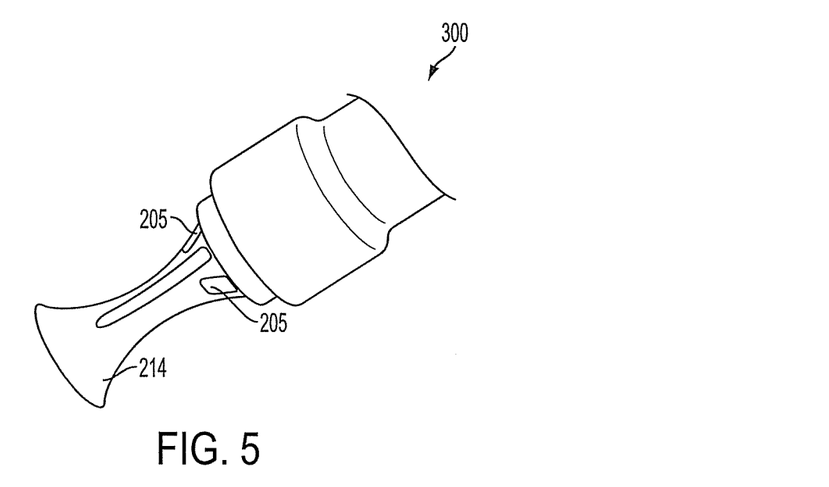
FIG. 5 is a perspective view of the assembled syringe and connector of FIG. 4.

FIG. 4 is a cross-sectional view of the connector of FIG. 2 assembled with the syringe of FIG. 3, in accordance with an exemplary embodiment. FIG. 5 is a perspective view of the assembly of FIG. 4.

To assemble connector 200 with syringe 300, aperture 215 is aligned with the well 312 of syringe 300. Connector 200 is then pushed into syringe well 312, and rotated until the protrusion that comprises locking feature 220 is properly aligned with groove 316. In an alternative embodiment, instead of one protrusion, there could be a plurality of protrusions. Preferably, two protrusions are present. In yet another alternative embodiment, a protrusion that is a continuous thread around the circumference of connector 200 may be present. Once the protrusion is aligned within groove 316, connector 200 continues to be rotated, and the protrusion moves along the path of groove 316, allowing connector 200 to move axially in the direction shown by arrow 230. The cross-sectional view in FIG. 4 shows the protrusion that comprises locking feature 220 fully engaged within groove 316, effectively locking connector 200 to syringe 300. A separating wall 330 within syringe 300 may operate as a stop point, or the diameters of the syringe tip 320 and sidewall 218 of interior conduit 216 may be such as to engage to effectively stop further axial movement. The connector may later be dismantled from the syringe by rotating the connector 200 in the opposite direction as it was inserted.

As shown in FIG. 4, separating wall 330 of syringe 300 separates a connecting chamber 340 with a fluid chamber 350. Connecting chamber 340 comprises the space defined by well 312. Within fluid chamber 350 is a stopper 360. Fluid contained within fluid chamber 350 is pressed downward, toward separating wall as by a plunger 118, until stopper 360 abuts separating wall 330. As the fluid is pushed toward separating wall 330, the fluid is forced through tip 320 of syringe 300, and then through conduit 216 of connector 200. In turn, with nipple 206 of connector 200 connected to a tube 120, the fluid continues to flow through tube 120 until it reaches the patient.

Because a user only touches gripping portion 214 to push connector 200 into syringe 300, the user need not ever touch internal conduit 216, keeping internal conduit 216 free from user-carried contamination. In addition, because conduit 216 lies within connector 200, conduit 216 is also less exposed to the environment while being attached to syringe 300. Similarly, syringe tip 320 lies within connecting chamber 340 and thus a user should not touch syringe tip 320 when attaching a connector to the syringe; likewise, syringe tip 320 will be less exposed to the environment when attached to a connector.

Figure 6:
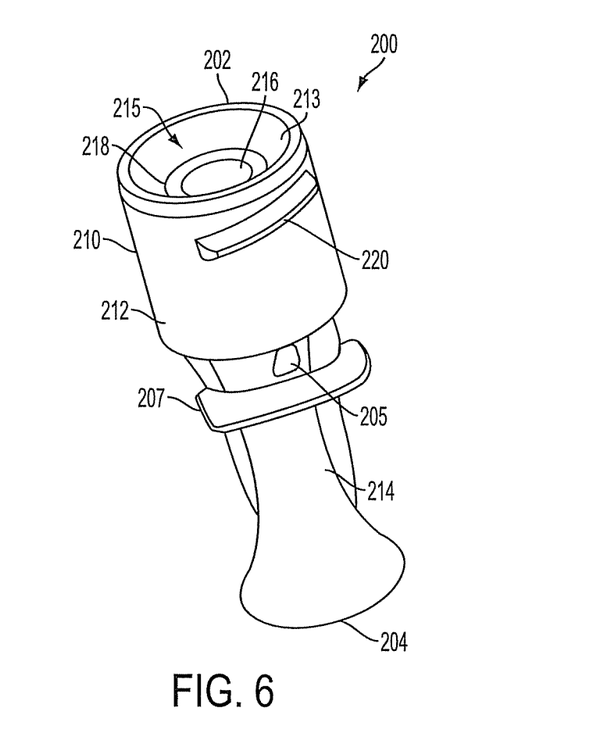
FIG. 6 is a perspective view of an alternative arrangement of a connector.

FIG. 6 is an alternate embodiment of a connector, such as the connector of FIG. 2. In FIG. 6, a ring 207 may be present on gripping portion 214, below vents 205. Ring 207 may serve as an additional gripping feature.

Figure 7:
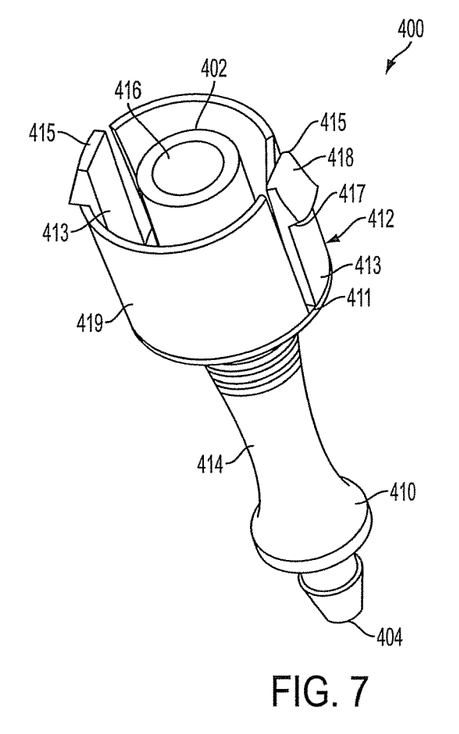
FIG. 7 is a perspective view of an alternative arrangement of a connector.

FIG. 7 is a perspective view of an alternative arrangement of a connector 400 that may be used with an enteral feeding system. Connector 400 includes an exterior surface 410, a first end 402, and a second end 404. The exterior surface 410 is comprised of two portions: an attachment portion 412 and a gripping portion 414.

Attachment portion 412 includes a collar 411 that extends axially from the exterior surface 410, a conduit 416, and a plurality of walls 419. Conduit 416 may take the shape of a tube with a bore defined therethrough. Conduit 416 extends through attachment portion 412 and gripping portion 414, and serves to conduct fluids therethrough. The bore of conduit 416 is sized to match an outer diameter of a syringe tip, such as the syringe 500 described below and shown in FIG. 8. Thus, conduit 416 serves as a female connector end at first end 402, sized to receive a syringe tip.

Figure 9:
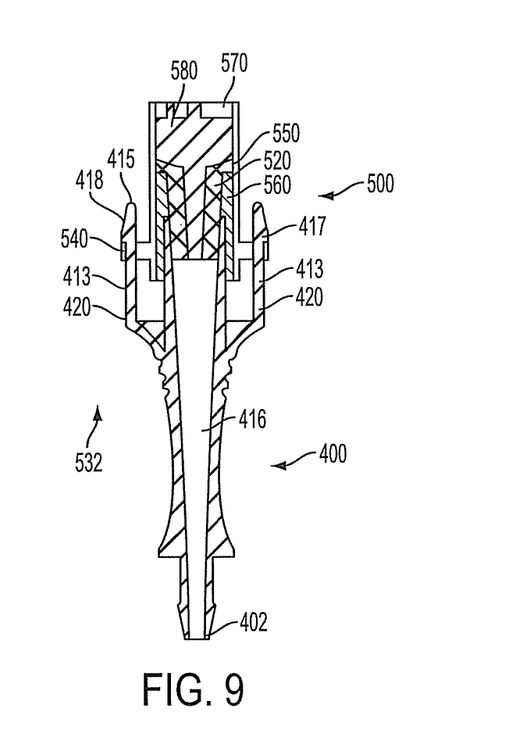
FIG. 9 is an assembled cross-sectional view of the connector of FIG. 7 within the syringe of FIG. 8, in accordance with another exemplary embodiment.

The exterior surface 410 of attachment portion 412 comprises a locking feature 420 (FIG. 9). In this embodiment, locking feature 420 comprises at least one flange 413 (here there are two), protruding substantially orthogonally from collar 411, each having an end 415. Each flange 413 has a ledge or shoulder 417 and a tapered portion or tab 418 near end 415. The taper of the tab 418 decreases in thickness as the tapered portion approaches end 415. The thickest part of tab 418 is at ledge 417.

Figure 8:
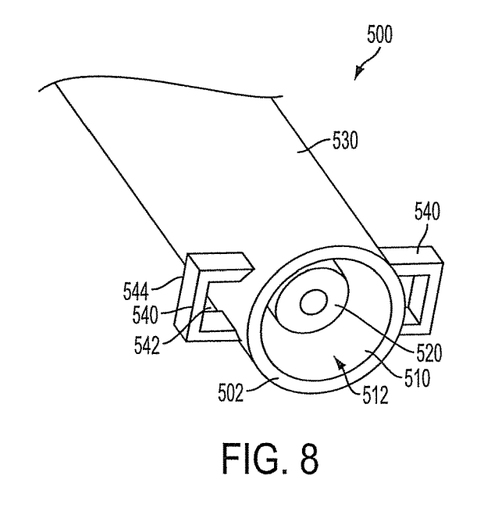
FIG. 8 is a partial, perspective view of an alternative arrangement of a syringe, such as the syringe of FIG. 1.

FIG. 8 is a partial, perspective view of the proximal end of a syringe 500. As can be seen in FIG. 8, at the proximal end 502 of syringe 500 is a well 512, defined by an interior surface 510. Interior surface 510 surrounds a syringe tip 520 that extends within well 512, but does not extend as far as proximal end 502. In an alternative embodiment, tip 520 may extend up to proximal end 502 or past the proximal end. Syringe 500 also comprises an exterior surface 530. Exterior surface 530 has at least one flange receptacle 540. Here, there are two receptacles 540, which are U-shaped. Each receptacle 540 includes a slot 542 and a top surface 544, which will engage the shoulder 417, as will be described.

Figure 10:
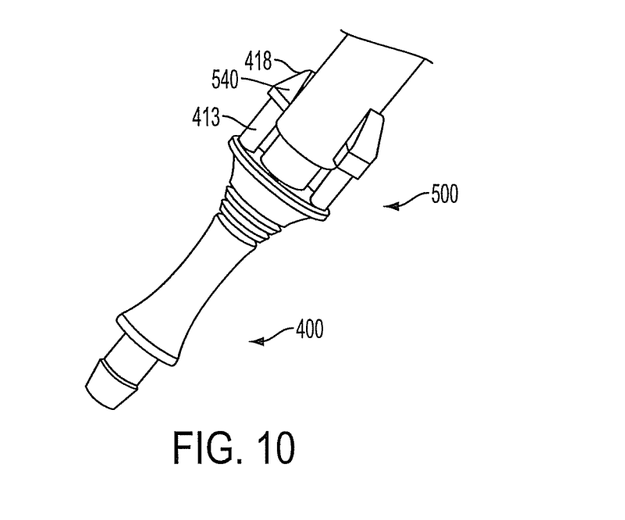
FIG. 10 is a perspective view of the assembled syringe and connector of FIG. 9.

FIG. 9 is a cross-sectional view of the connector of FIG. 7 assembled with the syringe of FIG. 8. FIG. 10 is a perspective view of the assembly of FIG. 9.

To assemble connector 400 with syringe 500, conduit 416 is aligned with the well 512 of syringe 500. As connector 400 is pushed into well 512, the tapered portion 418 of each flange 413 passes through the slot 542 in each receptacle 540. The taper comprises the smallest thickness when end 415 passes through slot 542. The taper presses the tab radially. After shoulder 417 passes through slot 542, the bottom surface of the shoulder 417 snaps over the top surface 544 of the receptacle 540.

These flanges 413 effectively lock connector 200 to syringe 300. Connector 400 is pushed axially in the direction of arrow 532, that is, toward a separating wall 550 within syringe 500. The flanges must be moved axially to disengage the connector 400.

As shown in FIG. 9, separating wall 550 of syringe 500 separates a connecting chamber 560 with a fluid chamber 570. Connecting chamber 560 comprises the space defined by aperture 512. Within fluid chamber 570 is a stopper 580 of a plunger. Fluid contained within fluid chamber 570 is pressed downward, toward separating wall 550, until the stopper 580 abuts separating wall 550. As the fluid is pushed toward separating wall 550, it is forced through tip 520 of syringe 500, and then through conduit 416 of connector 400. In turn, a nipple formed on first end 402 of connector 400 is connected to an enteral tube, through which the fluid flows until it reaches the patient.

By using gripping portion 514 to push connector 400 into syringe 500, a user does not need to touch conduit 416, thus keeping conduit 416 free from user-carried contamination. Similarly, syringe tip 520 lies within well 512, and is likewise protected from user-contact. Walls 419 and flanges 413 keep a user's fingers from contacting the conduit 416.

Figure 11:
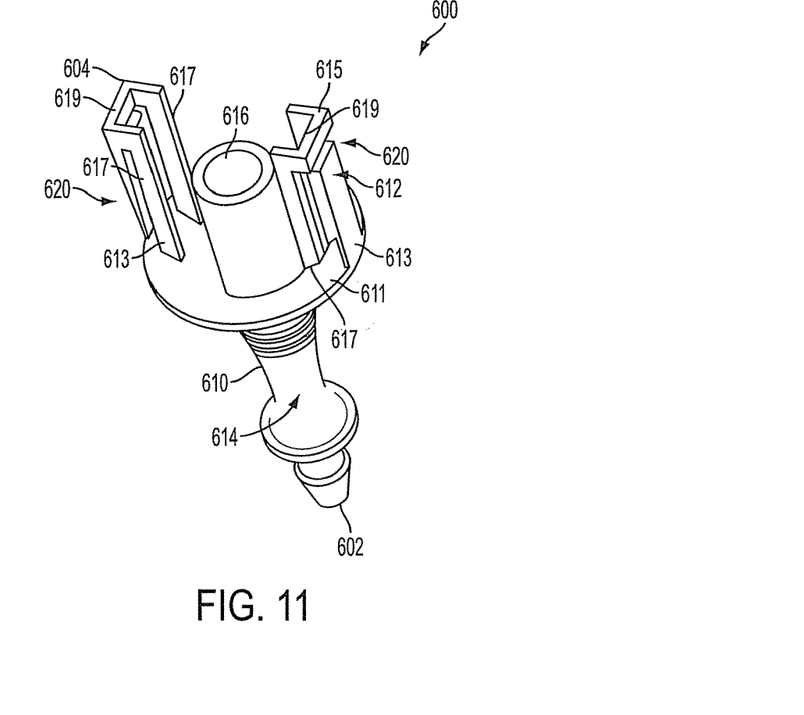
FIG. 11 is a perspective view of an alternative arrangement of a connector.

FIG. 11 is a perspective view of an alternative arrangement of a connector 600 that may be used with an enteral feeding system. Connector 600 includes an exterior surface 610, a first end 602, and a second end 604, and defines an attachment portion 612 and a gripping portion 614.

Attachment portion 612 includes a collar 611 that extends axially from the exterior surface 610, and a conduit 616. Conduit 616 may take the shape of a tube with a bore defined therethrough. Conduit 616 extends through attachment portion 612 and gripping portion 614, and serves to conduct fluids therethrough. The bore of conduit 616 is sized to match an outer diameter of a syringe tip, such as the syringe described below and shown in FIG. 12. Thus, conduit 616 serves as a female connector end, sized to receive a syringe tip.

The exterior surface 610 of attachment portion 612 has a locking feature 620. In this embodiment, locking feature 620 comprises an extension 613 protruding substantially orthogonally from collar 611, and having an end 615. Locking feature 620 also comprises a flange receptacle 615 having opposed sidewalls 617 which parallel the extension 613, and a top edge piece 619.

Figure 12:
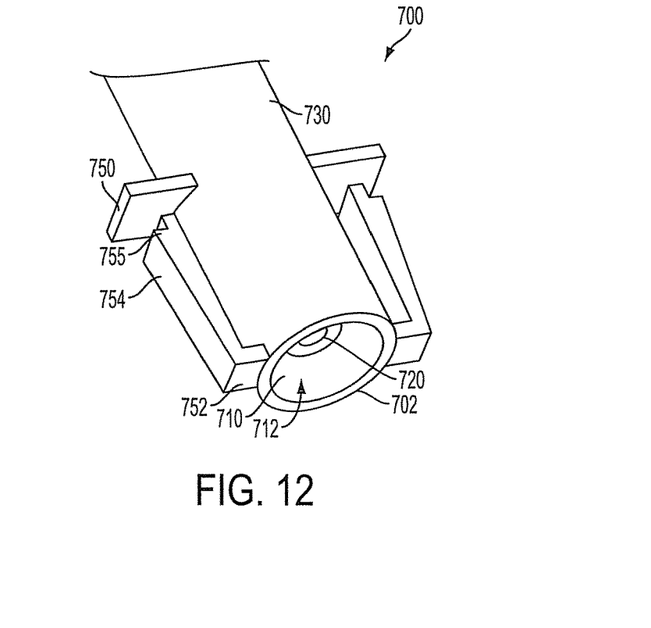
FIG. 12 is a partial, perspective view of the proximal end of another syringe.

FIG. 12 is a partial, perspective view of the proximal end of a syringe 700, such as the type of syringe of the type of FIG. 1. As can be seen in FIG. 12, however, at the proximal end 702 of syringe 700 is a well 712, defined by an interior surface 710. A syringe tip 720 extends within well 712, but does not extend as far as proximal end 702. Syringe 700 also has an exterior surface 730. Exterior surface 730 comprises at least one protruding flange 754; here there are two, on opposite sides. In addition, a flange 754 extends along the side of the exterior surface 730, connected thereto by a section 752. Section 752 extends generally orthogonally from exterior surface 730 at or near proximal end 702. The flange 754 extends generally orthogonally from first section 752, toward the distal end of syringe 700, and can flex relative to the exterior surface 730.

Figure 13:
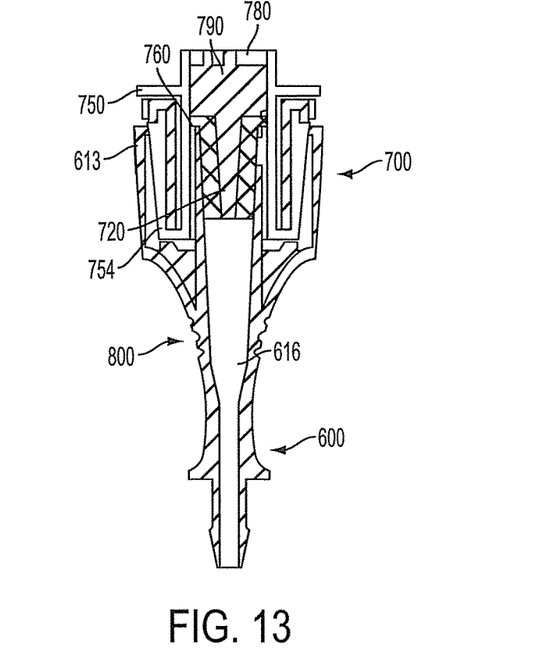
FIG. 13 is an assembled cross-sectional view of the connector of FIG. 11 within the syringe of FIG. 12, in accordance with exemplary embodiments.
Figure 14:
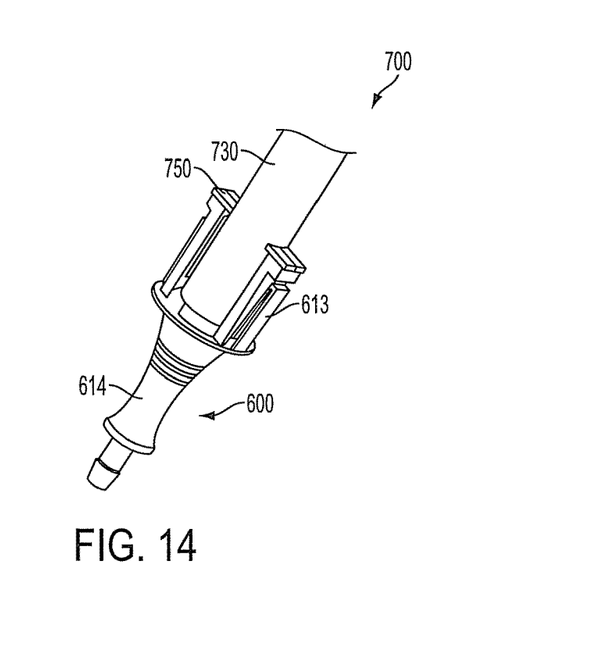
FIG. 14 is a perspective view of the assembled syringe and connector of FIG. 13.

FIG. 13 is a cross-sectional view of the connector of FIG. 11 assembled with the syringe of FIG. 1. FIG. 14 is a perspective view of the assembly of FIG. 13.

To assemble connector 600 with syringe 700, aperture 616 is aligned with the well 712 of syringe 700. As connector 600 is pushed into well 712, the extension 613 contacts the flange 754, which fits and travels within the flange receptacle 615, framed by the sidewalls 617 and edge piece 619. Flange 754 travels within the receptacle until engaging in a snap fit with the bottom of top edge piece 619 along shoulder 755 of the flange 754. Here, like the previous embodiment, a user must push the flange out of engagement in order to remove the connector 600.

As shown in FIG. 13, separating wall 760 of syringe 500 separates a connecting chamber 770 with a fluid chamber 780. Within fluid chamber 780 is a stopper 790 of a plunger. Fluid contained within fluid chamber 780 is pressed downward, toward separating wall 760, until the stopper 790 abuts separating wall 760. As the fluid is pushed toward separating wall 760, it is forced through tip 720 of syringe 700, and then through conduit 616 of connector 600. In turn, a nipple formed on end 602 of connector 600 is connected to an enteral feeding tube, through which the fluid flows until it reaches the patient.

Because a user need only touch gripping portion 614 to push connector 600 into syringe 700, the user does not ever have to touch conduit 616, keeping conduit 616 free from user-contamination. Similarly, syringe tip 720 lies within well 712, and thus a user need not touch syringe tip 720 when attaching a connector to the syringe, protecting tip 720.

Instead of attaching to a syringe, connectors 200, 400, and 600 may attach to an extension set or extension tubing.

Figure 15:
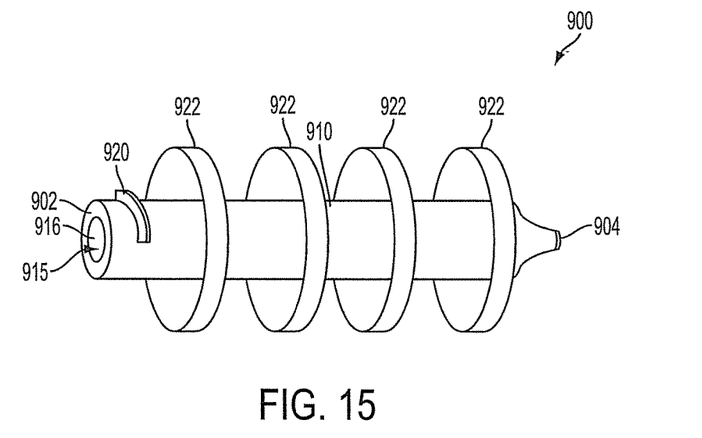
FIG. 15 is a perspective view of an alternative embodiment for a connector.

FIG. 15 shows a perspective view of an alternative embodiment for a connector 900. Connector 900 has an exterior surface 910 and an aperture 915 defining an internal conduit 916 that extends from a first end 902 to a second end 904. Internal conduit 916 may take the shape of a tube with a bore defined therethrough.

Attachment features, such as the attachment features described with relation to FIGS. 2, 7, and 11 may be present on connector 900. As an example, connector 900 is shown with a locking mechanism 920, which is identical to locking mechanism 220 as defined with relation to FIG. 2.

As seen in FIG. 15, a plurality of axially extending ribs 922 are present around the circumference of exterior surface 910. These ribs may be gripped by the user when manipulating connector 900. A user handling the connector thus need not contact the ends, reducing the risk of contaminating the conduit 916.

Figure 16:
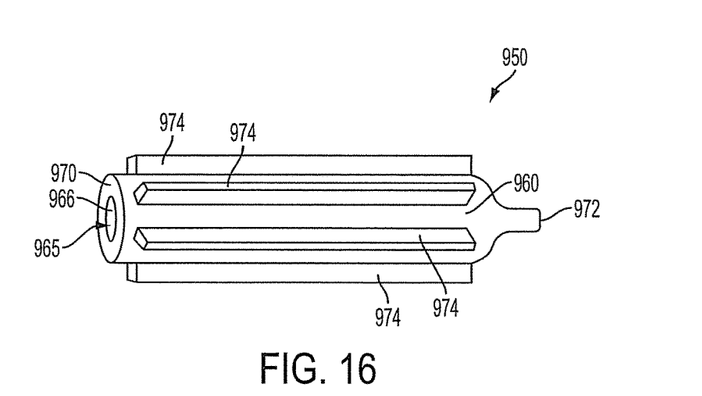
FIG. 16 is a perspective view of another alternative embodiment for a connector.

FIG. 16 shows a perspective view of an alternative embodiment for a connector 950. Connector 950 has an exterior surface 960 and an aperture 965 defining an internal conduit 966 that extends from a first end 970 to a second end 972. Internal conduit 966 may take the shape of a tube with a bore defined therethrough.

As seen in FIG. 16, a plurality of protrusions 974 extend along the length of connector 950, in the form of longitudinal ribs. Protrusions 974 may extend from first end 970 to near second end 972, or may be shorter. Any of these protrusions may be gripped by the user when manipulating connector 950. A user handling the connector thus need not contact the ends, reducing the risk of contaminating the conduit 966. In this embodiment, attachments are made through a standard interference (slip) fit, as the novel aspect here is the "no-touch" feature.

Figure 17:
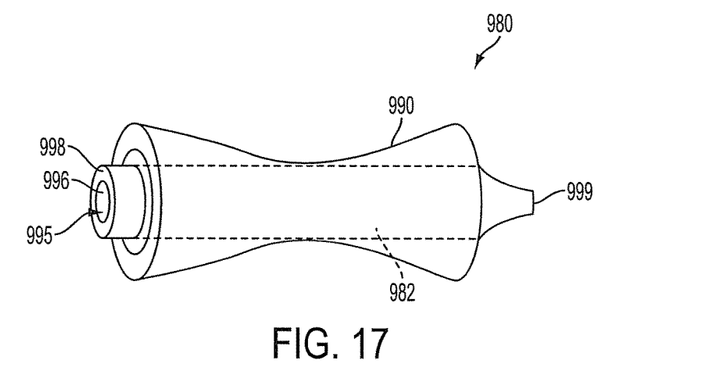
FIG. 17 is a perspective view of yet another alternative embodiment for a connector.

FIG. 17 shows a perspective view of an alternative embodiment for a connector 980. Connector 980 has an exterior surface 990 and an aperture 995 defining an internal conduit 996 that extends from a first end 998 to a second end 999. Internal conduit 996 may take the shape of a tube with a bore defined therethrough. The connector 980 does not comprise a novel attachment feature, but instead has a novel grip portion 982. Connector 980 is attached to a via slip or interference fits.

Various exemplary embodiments and methods have been described above. Those skilled in the art will understand, however, that changes and modifications may be made to those examples without departing from the scope and spirit of the present invention. Additional and/or different features may be present in some embodiments of the present invention.

What is claimed is:

1. An enteral feeding system comprising:
a connector having a first end comprising an aperture having a diameter, a second end comprising an element for attachment to an enteral tube, an exterior sidewall and an interior sidewall defining an internal conduit, wherein the interior sidewall is arranged parallel to the exterior sidewall, wherein a first end of the exterior sidewall extends past a first end of the internal conduit and wherein the internal conduit has a diameter that is less than the diameter of the aperture, wherein the internal conduit is within the connector between the first and second ends, and a first part of a locking mechanism; and
a syringe having a tip, with a wall surrounding the tip forming a well, and a second part of the locking mechanism formed adjacent the tip on the wall;
wherein the tip of the syringe mates and is in fluid communication with the internal conduit when the syringe is inserted within the aperture, and wherein the first and second parts of the locking mechanism engage to releasably lock the connector to the syringe,
wherein the exterior sidewall has a shoulder that extends radially relative to the interior sidewall and defines a second end of the aperture, wherein the connector further comprises at least one vent arranged through the shoulder of the exterior sidewall, the at least one vent configured to keep an inside of the connector dry.

2. The enteral feeding system of claim 1, wherein the internal conduit is surrounded by the exterior sidewall and is accessible at the ends within the exterior sidewall.

3. The enteral feeding system of claim 1, wherein an exterior of the syringe is handled by a user when the user attaches the tube to the syringe, and the internal conduit is generally protected against contact by the user.

4. The enteral feeding system of claim 1, wherein the first part of the locking mechanism is a protrusion on the exterior sidewall, and the second part of the locking mechanism is a groove formed on the well within which the first part slidably fits.

5. The enteral feeding system of claim 1, wherein the locking mechanism is a latch engaging within a receptacle.

6. The enteral feeding system of claim 1, wherein the locking mechanism comprises a positive latching arrangement that, when engaged, prevents disengagement of the connector without radial movement of part of the locking mechanism relative to another part.

7. An enteral feeding system, comprising:
a connector having a first end comprising an aperture having a diameter, a second end, an exterior sidewall, an interior sidewall defining an internal conduit, wherein the interior sidewall is arranged parallel to the exterior sidewall, wherein a first end of the exterior sidewall extends past a first end of the internal conduit and wherein the internal conduit has a diameter that is less than the diameter of the aperture, wherein the internal conduit is within the connector between the first and the second ends; and
a syringe having a tip, with a wall surrounding the tip forming a well, the wall defining an exterior surface; wherein the exterior surface of the syringe is configured to be handled by a user when the user attaches the connector to the syringe, and wherein the syringe tip, when inserted within the aperture, communicates with the internal conduit;
wherein the exterior sidewall has a shoulder that extends radially relative to the interior sidewall, wherein the connector further comprises at least one vent arranged through the shoulder, the at least one vent configured to keep an inside of the connector dry.

8. The enteral feeding system of claim 7, wherein the syringe tip is inserted into the aperture at the first end of the connector and remains fixed within the aperture with a slip fit.

\* \* \* \* \*